United States Patent [19]

Graham, Jr. et al.

[11] 4,254,098

[45] Mar. 3, 1981

[54] COMPOSITION FOR PROPHYLACTIC TREATMENT OF PINKEYE

[75] Inventors: Joseph A. Graham, Jr., Milo, Iowa; Clair R. Hibbs, Albuquerque, N. Mex.

[73] Assignees: Clair M. Hibbs; Kenneth R. Wilburn; Max. A. Mekus, ; part interest to each

[21] Appl. No.: 115,666

[22] Filed: Jan. 28, 1980

[51] Int. Cl.³ .................... A61K 39/02; A61K 9/22
[52] U.S. Cl. .................... 424/14; 128/260; 424/19; 424/22; 424/28; 424/92
[58] Field of Search .............. 424/14, 16, 19–22, 424/28, 92; 128/260

[56] References Cited

U.S. PATENT DOCUMENTS

| B 520,277 | 2/1976 | Hisuchi et al. | 128/260 |
|---|---|---|---|
| 3,197,373 | 7/1965 | Jackson | 424/92 |
| 3,302,646 | 2/1967 | Behney | 128/260 |
| 3,401,219 | 9/1968 | Zeissig | 424/92 |
| 3,853,990 | 12/1974 | Madigan et al. | 424/92 |
| 3,870,791 | 3/1975 | Haddad et al. | 424/22 |
| 3,960,150 | 6/1976 | Hussain et al. | 128/260 |
| 3,962,414 | 6/1976 | Michaels | 424/19 |
| 3,986,510 | 10/1976 | Hisuchi et al. | 128/260 |
| 4,186,184 | 1/1980 | Zaffaroni | 424/14 |
| 4,201,210 | 5/1980 | Hughes et al. | 128/260 |

*Primary Examiner*—Shep K. Rose
*Attorney, Agent, or Firm*—Cushman, Darby & Cushman

[57] ABSTRACT

Attenuated *Moraxella bovis* is applied directly to the eye of cattle to immunize the eye against the occurrence of pinkeye.

9 Claims, No Drawings

COMPOSITION FOR PROPHYLACTIC TREATMENT OF PINKEYE

The invention is directed to prophylactic treatment of "pinkeye" (infectious keratoconjunctivitis) which is a disease of the eyes of cattle caused by the bacteria *Moraxella bovis*.

Pinkeye is highly contagious and can be transmitted rapidly throughout a herd. The disease is characterized by an acute to chronic inflammation of the eye and impairs the sight of the animal. As it affects cattle of all ages and breeds and as it is debilitating, pinkeye causes enormous financial loss in the cattle industry.

Treatment of the diseased animal is impractical. It is difficult to administer medical treatment to a diseased animal, particularly if it is in a range herd. Curative results of medical treatment are not generally satisfactory. Infection in one eye apparently immunizes an animal against the recurrence of pinkeye in the affected eye, although the unaffected eye is not immunized against the disease and thus may become infected in later seasons. Thus, prophylactic treatment is practically beneficial.

SUMMARY OF THE INVENTION

The invention is directed to providing cellular immunity in the lining of the eyelids of cattle to prevent infection thereof by the *Moraxella bovis* bacteria.

Antibodies induced by the pinkeye disease itself and present in the tears of both eyes of the cow, even when only one of the eyes was affected by pinkeye, do not provide immunity to pinkeye infection of the undiseased eye.

Thus, the invention is directed to the production of modified *Moraxella bovis* used as a medicament in the prophylactic treatment of cattle to immunize the cattle against pinkeye.

DESCRIPTION OF THE INVENTION

The invention is directed to the production of attenuated *Moraxella bovis* which in its unattenuated form causes pinkeye and to its use as a prophylactic in immunizing cattle against pinkeye. Particularly, the discovery of the invention resides in the induction of local cell immunity to pinkeye in the eye itself. A strain of *Moraxella bovis* which causes pinkeye has previously been deposited and has received the number A.T.C. 10,900; the characteristics of this strain of *Moraxella bovis* are described in U.S. Pat. No. 3,197,373, which is incorporated by reference herein. Isolation of the *Moraxella bovis* can be accomplished simply by swabbing the eyes of cattle sustaining active cases of pinkeye and identifying the strain by conventional methods described, for instance, in Bergey's Manual of Determinative Bacteriology.

Unlike descriptions of U.S. Pat. Nos. 3,197,373; 3,401,219 and 3,853,990 which involve killing the *Moraxella bovis* bacteria used in the treatment of pinkeye, attenuation of *Moraxella bovis*, in accordance with the present invention, does not result in killing the bacteria. Rather, in accordance with the present invention, modification of *Moraxella bovis* simply reduces the virulence of disease producing capabilities by processes known as attenuation.

Attenuation of bacteria generally can be accomplished by heating the bacteria to just below their thermal death point or by exposing them to marginally sublethal concentrations of inactivating chemicals. Other attenuation methods involve culturing bacteria in unfavorable growth media or at unfavorable temperatures or in unusual atmospheres or under conditions in which a shortage of nutrients is maintained.

Presently, in accordance with the invention, attenuation of *Moraxella bovis* is accomplished by a heat treatment of pure cultures of *Moraxella bovis* which are isolated from active cases of pinkeye (infectious bovine keratoconjunctivitis). For the heat treatment in accordance with the invention, isolates of unattenuated culture of *Moraxella bovis* are admixed with bovine heart infusion. The bovine heart infusion broth may be obtained commercially, for instance from Difco Laboratories of Detroit, Michigan. Conveniently, the concentration of unattenuated culture of *Moraxella bovis* in the heart infusion broth is $10^8$/ml.

Attenuation in accordance with the invention is accomplished by a heat treatment which involves two stages of serial temperature changes. In the first stage, the culture-broth mixture is subjected to serially decreasing temperature changes starting at a temperature of 37° C. That is, starting from a temperature of 37° C., the temperature is reduced 0.5° C. until after 10 serial temperature reductions the temperature of the heat treatment is 32° C. In the second subsequent stage, the culture is subjected to serially increasing temperature changes starting from 38° C., and the temperature treatment is continued by serially increasing the temperature 0.5° C. twenty times, up to 48° C. The time period required for attenuation is approximately 30 days, and each serial temperature change is of substantially equal duration; that is, each serial temperature change of 0.5° C. is undertaken every two days.

The attenuated culture is then isolated by conventional methods. The attenuated culture is isolated from the bovine heart infusion broth by centrifugation and loop isolation and then transferred to a protein-free salts medium.

Alternatively, the *Moraxella bovis* can be attenuated by a different process. That is, the *Moraxella bovis* can be mutagenized by the modified methods of Adelberg et al and Oeschger and Berlyn to obtain colonies dependent on antibiotics and resistant to antibiotics according to a method for attenuating bacteria and rendering bacteria simultaneously streptomycin dependent and streptomycin resistant described by B. D. Wei and G. R. Carter in the American Journal of Veterinary Research, Volume 39, No. 9, pages 1534 through 1537 (September 1978). According to this method, a four-hour logarithmic phase culture (10 ml.) grown in a suitable medium is centrifuged at 20,000 xg for ten minutes. The solid material gathered from the centrifuge process is resuspended in a buffer. The cells in the buffer are mutagenized at a final concentration of NTG at 0.1 milligram/ml. for 15 minutes at 37° C. The suspension is centrifuged, washed with broth, centrifuged again, suspended in 100 ml. of a suitable media and then incubated for 12 hours. The culture is again centrifuged at 20,000 xg for ten minutes and suspended in only 1 ml. of medium. Ten streptomycin augur plates containing 100 millimicrograms of streptomycin/ml. are inoculated and incubated for 48 hours. Each of the ten spread plates is replicated by the method of Lederberg and Lederberg first onto a plain medium then onto one with 100 millimicrograms of streptomycin/ml. The plates are incubated for 48 hours. Colonies growing better on the streptomycin medium than on the plain medium are individually picked with a straight wire, one-half being placed on a plain medium and one-half being placed on a streptomycin medium in order to test dependency. Colonies growing exceptionally well on the streptomycin medium but not at all on the plain medium are antibiotic, streptomycin, dependent.

The attenuated culture may be formulated in various forms for application to the eyes, for the prophylactic treatment of pinkeye. Preferably, however, the attenuated culture is formulated as a time release formulation, in the form of an ocular insert. The ocular insert is preferably placed between the lower eyelid and the eyeball in the conjunctival sac. Such an ocular insert is formed from a drug release rate controlling material which is the matrix of the ocular insert and which is permeable to the passage of the attenuated *Moraxella bovis*. Drug release rate controlling materials for ocular inserts and methods for producing the ocular inserts from them are known in the art and are described in U.S. Pat. Nos. 3,618,604; 3,626,940; 3,867,519; 3,961,628; 3,991,759; 3,993,071; 3,995,635; 4,014,334; and 4,014,335, all of which are incorporated by reference herein. The drug release rate controlling materials of the matrix of ocular inserts are generally flexible naturally occurring or synthetic polymer type materials that are biologically inert, bioerodible, non-allergenic and insoluble in tear liquid. Preferably sodium alginate is used which can be procured from the Kelco Co. of Kentucky and is marketed as "Keltone".

Cattle about to be immunized to pinkeye may already be in any stage of the disease. Since immunity and/or resistance to pinkeye may take several days, inflammation may occur before protection is induced.

Thus, in addition, to treating the eye directly with the attenuated *Moraxella bovis* pretreatment of the eye with an antibiotic may be advantageous. Thus, the ocular insert may include an antibiotic in addition to the attenuated *Moraxella bovis*. For instance, the antibiotic may be streptomycin or the like. The attenuated *Moraxella bovis* may be an attenuated streptomycin dependent strain of *Moraxella bovis*. The ocular insert is designed to release the antibiotic, for instance streptomycin, in a first period, e.g. approximately 3 days and then, to release the attenuated *Moraxella bovis*, in a second period of approximately 3 days.

Following the treatment, the eye may be treated with sulfadiazine, or other drugs or antibiotics to which *Moraxella bovis* is sensitive, to eliminate the *Moraxella bovis* and any field strains that have become resistant to the antibiotic. Alternatively, the eye may be treated, subsequent to treatment with *Moraxella bovis*, with a saprophyte known to be antagonistic to *Moraxella bovis*. Thus, the ocular insert can be designed to contain, in addition to attenuated *Moraxella bovis*, an antibiotic and sulfadiazine or a saprophyte which is antagonistic to *Moraxella bovis*, whereby the design of the ocular insert allows the sequential release of optionally the antibiotic, then release of attenuated *Moraxella bovis* and lastly and optionally either sulfadiazine or a saprophyte antagonistic to *Moraxella bovis*.

Preferably, for reasons of practicality, the sulfadiazine or the saprophyte when employed, are included in the ocular insert. Thus in one embodiment of the invention, the ocular insert includes the antibiotic, the attenuated *Moraxella bovis* and at least the sulfadiazine or the saprophyte and is designed to release the sulfadiazine or the saprophyte after release of the attenuated *Moraxella bovis*.

The treatment to immunize cattle against pinkeye will take several days and can include a pretreatment as well as post-treatment. The amount of attenuated *Moraxella bovis*, administered to the eyes to immunize the cattle against pinkeye, in the treatment stage, can vary proportionally to from 0.1 to 1 ml. of attenuated culture attenuated and grown at the aforementioned concentration of $10^8$ per ml, based on the dilution in the bovine heart infusion broth.

What is claimed is:

1. A medicament for the treatment of the eyes of bovine comprising a biologically inert, bioerodible, nonallergenic, insoluble carrier and an amount of an attenuated strain of *Moraxella bovis* effective to induce immunity to pinkeye in said cattle, wherein the unattenuated strain of said *Moraxella bovis* causes pinkeye in bovine.

2. The medicament of claim 1, which includes an antibiotic.

3. The medicament of claim 1 or 2 in the form of an ocular insert in which the carrier is release rate controlling material and is permeable to the passage of attenuated *Moraxella bovis*.

4. The method of inducing in bovine an immunity to pinkeye which is infectious keratoconjunctivitis, comprising applying to the bovine eye which eye has been unaffected by pinkeye disease, a composition comprising an amount of an attenuated strain of *Moraxella bovis* which is effective to immunize said eye to pinkeye, wherein the unattenuated strain of said *Moraxella bovis* causes pinkeye.

5. The method of claim 4, wherein said composition is in the form of an ocular insert formed of a matrix of a release rate controlling naturally occurring or synthetic material which is biologically inert, bioerodible, non-allergenic and insoluble in tear fluid and wherein said ocular insert is disposed in the conjunctival sac.

6. The method of claim 4 which further includes the step of treating said eye with an antibiotic prior to applying said composition.

7. The method of claim 4, wherein the attenuated *Moraxella bovis* has been attenuated by subjecting unattenuated *Moraxella bovis* to a heat treatment of serial temperature changes over a range of temperatures of from about 32° C. to about 48° C.

8. The method of claim 7, wherein the heat treatment is undertaken in two stages wherein in one stage the temperature is decreased to about 32° C. and in another stage the temperature is increased to about 48° C.

9. The method of claim 7, wherein said attenuated *Moraxella bovis* is antibiotic dependent.

* * * * *